(12) United States Patent
Fasching et al.

(10) Patent No.: US 8,658,042 B2
(45) Date of Patent: Feb. 25, 2014

(54) MICROPLATE CARRIER HAVING MAGNETS

(75) Inventors: Gerhard Fasching, Hallein (AT); Teresa Hruschka, Salzburg (AT); Lutz Niggl, Waging (DE); Patrick Niklaus, Salzburg (AT)

(73) Assignee: Tecan Trading AG, Mannedorf (CH)

( * ) Notice: Subject to any disclaimer, the term of this patent is extended or adjusted under 35 U.S.C. 154(b) by 474 days.

(21) Appl. No.: 12/198,210

(22) Filed: Aug. 26, 2008

(65) Prior Publication Data
US 2009/0064800 A1    Mar. 12, 2009

Related U.S. Application Data

(60) Provisional application No. 60/969,236, filed on Aug. 31, 2007.

(30) Foreign Application Priority Data

Aug. 31, 2007    (CH) ...................................... 1360/07

(51) Int. Cl.
B01L 3/00    (2006.01)
G01N 31/20    (2006.01)
B03C 1/30    (2006.01)

(52) U.S. Cl.
USPC ............ 210/695; 210/222; 422/552; 422/534

(58) Field of Classification Search
USPC .......... 210/222, 223, 695; 422/102, 104, 407, 422/551, 552, 553, 569, 534; 436/177–178
See application file for complete search history.

(56) References Cited

U.S. PATENT DOCUMENTS

| 4,272,510 | A | * | 6/1981 | Smith et al. ................... 427/598 |
| 4,438,068 | A | * | 3/1984 | Forrest .......................... 422/430 |
| 4,988,618 | A | | 1/1991 | Li et al. |
| 5,290,521 | A | * | 3/1994 | DeStefano, Jr. ................ 422/99 |
| 5,458,785 | A | * | 10/1995 | Howe et al. .................... 210/695 |
| 5,541,072 | A | * | 7/1996 | Wang et al. .................... 435/7.21 |
| 5,609,826 | A | * | 3/1997 | Cargill et al. ................... 422/99 |
| 5,779,907 | A | | 7/1998 | Yu |

(Continued)

FOREIGN PATENT DOCUMENTS

| EP | 0528708 | 2/1993 |
| EP | 0589636 | 3/1994 |

(Continued)

Primary Examiner — David C Mellon
(74) Attorney, Agent, or Firm — Notaro, Michalos & Zaccaria P.C.

(57) ABSTRACT

Relates to a microplate carrier (1) for a microplate (2), in whose wells (3) magnetic particles (5), which are suspended in a liquid (4), with or without samples adhering thereto are located, the microplate carrier (1) comprising permanent magnets (6) generating magnetic fields which are implemented to collect and retain the magnetic particles (5) on the floor (14) and/or on the walls (7) of the wells (3) of this microplate (2). The microplate carrier (1) according to the invention is characterized in that it comprises two permanent magnets (6) situated diametrically opposite in relation to the well (3) for each well (3) of the microplate (2), which have the same polarity directed toward the well (3) and whose magnetic axis (25) is at least essentially perpendicular to the footprint of the microplate (2) to be placed. A corresponding method based on the use of the microplate carrier (1) is also disclosed.

15 Claims, 1 Drawing Sheet

(56) References Cited

U.S. PATENT DOCUMENTS

| | | | |
|---|---|---|---|
| 6,406,671 B1 * | 6/2002 | DiCesare et al. | 422/101 |
| 6,485,690 B1 * | 11/2002 | Pfost et al. | 422/102 |
| 6,514,415 B2 * | 2/2003 | Hatch et al. | 210/695 |
| 6,514,416 B1 | 2/2003 | Harradine et al. | |
| 6,645,431 B2 * | 11/2003 | Astle | 422/99 |
| 6,776,174 B2 * | 8/2004 | Nisson et al. | 134/104.4 |
| 7,169,578 B2 * | 1/2007 | Wang et al. | 435/30 |
| 2002/0070173 A1 * | 6/2002 | Otto et al. | 210/695 |
| 2002/0110825 A1 * | 8/2002 | Spicer et al. | 435/6 |
| 2006/0081539 A1 | 4/2006 | Safar et al. | |

FOREIGN PATENT DOCUMENTS

| | | |
|---|---|---|
| GB | 2 300 258 | 10/1996 |
| JP | 2000-292426 A | 10/2000 |
| JP | 2004-283728 A | 10/2004 |
| JP | 2005-233931 | 9/2005 |
| WO | WO 92/05443 | 4/1992 |
| WO | WO 02/055206 | 7/2002 |
| WO | WO 03/090897 | 11/2003 |

\* cited by examiner

MICROPLATE CARRIER HAVING MAGNETS

RELATED PATENT APPLICATIONS

This patent application claims priority of the U.S. provisional application No. 60/969,236 as well as from the Swiss patent application No. 01360/07, both filed on Aug. 31, 2007. The entire content of these two priority defining applications is incorporated herein by explicit reference for any purpose.

RELATED FIELD OF TECHNOLOGY

The invention relates to a microplate carrier for microplates, in whose wells magnetic particles, which are suspended in a liquid, with or without samples adhering thereto are located. The microplate carrier comprises permanent magnets which generate magnetic fields, which are implemented to collect and retain the magnetic particles on the floor and/or on the walls of the wells of this microplate. Cannulas of a microplate washing device for suctioning at least a part of the liquid may thus be lowered into the wells, for example, without these cannulas contacting the concentrated magnetic particles. The invention additionally relates to a corresponding method.

RELATED PRIOR ART

Many, partially also automated devices are known which are used for separating magnetic particles from liquids. The magnets used are annular magnets situated directly below each well of a microplate, for example. These annular magnets have the disadvantage, however (cf., for example, EP 0 589 636 B1), that only a specific type of microplates (e.g., having V floor or round floor) may be used in an optimized way. Different configurations of magnetic plates which approach the wells of a microplate or other containers from the side are also known (cf., for example, WO 02/055206 A2).

Other devices comprise permanent magnets which are placed coaxially under each well of a microplate. However, such devices have the disadvantage that the entire floor of the well, or at least the lowest point (and thus the preferred suction location) in this well is occupied by concentrated magnetic particles. A relatively large residual volume of liquid thus results in the well, which may not be suctioned off without significant loss of magnetic particles. In addition, this residual volume results in inadequate liquid exchange and thus inefficient washing.

Carriers for microplates according to the species are known, for example, from U.S. Pat. No. 5,779,907. This document discloses a magnetic separator for microplates which is implemented as a carrier for microplates in a relatively fixed position and has a plurality of cylindrical magnets which are situated in a 4×6 array. These magnets penetrate from below into the intermediate spaces between each four wells of a microplate and do not come into contact with the liquids in the wells of this microplate. The magnets cause a concentration of magnetic particles suspended in a liquid in the wells on the walls of these wells, so that the cannulas of a washing unit may be lowered into the wells without these cannulas contacting the concentrated magnetic particles.

Similar carriers are also known from GB 2 300 258, which discloses a magnetic separating device, which comprises a 96-well microplate and a transparent baseplate. A plurality of magnets is fastened to this baseplate, which is adapted to the size of the area ("footprint") of the microplate. The magnets are distributed symmetrically on the baseplate, so that each of these magnets is enclosed by four wells of the microplate. The magnets cause magnetic particles suspended in a liquid in the wells to be concentrated on the walls of these wells, so that the liquid contents of the wells may be illuminated and visually examined in a reader.

These two carriers for microplates known from the prior art have the disadvantage that the concentration of the magnetic particles occurs at different points in the wells of a microplate, because of which the automation of a washing process is made more difficult, for example. For automated suctioning of liquid, only the center of the floor of the well is perfectly accessible. If microplates having flat floor wells are used, central suctioning results in an annular residual volume which impairs the washing efficiency, however.

OBJECTS AND SUMMARY OF THE PRESENT INVENTION

The object of the present invention is to suggest an alternative device which eliminates or at least minimizes the disadvantages known from the prior art.

The stated object is achieved according to a first aspect by the features herein disclosed, in that a microplate carrier for a microplate is suggested. Magnetic particles, which are suspended in a liquid, with or without samples adhering thereto are located in the wells of this microplate. The microplate carriers comprise permanent magnets generating magnetic fields, which are implemented to collect and retain the magnetic particles on the floor and/or on the walls of the wells of this microplate. The microplate carrier according to the invention is characterized in that it comprises two permanent magnets situated diametrically opposite in relation to the well for each well of the microplate, which have the same polarity directed toward the well and whose magnetic axis is at least essentially perpendicular to the footprint of the microplate to be placed.

The stated object is achieved according to a second aspect by the features herein disclosed, in that a method for processing microplates is suggested. In this method for processing microplates, in whose wells magnetic particles, which are suspended in a liquid, with or without samples adhering thereto are located, such a microplate is placed on a microplate carrier which comprises permanent magnets generating magnetic fields, using which the magnetic particles are collected and retained on the floor and/or on the walls of the wells. The method according to the invention is characterized in that the microplate carrier provides two permanent magnets situated diametrically opposite in relation to the well for each well of the microplate, which have the same polarity directed toward the well and whose magnetic axis is at least essentially perpendicular to the footprint of the microplate to be placed.

Additional preferred and inventive features result from the dependent claims.

Advantages of the microplate carrier according to the invention comprise the following:

For all microplate types (whether their wells have a flat, round, or V floor, or whether the wells are implemented as conical, pyramidal, or as truncated cones), an at least essentially particle-free space which extends transversely to an axis connecting the two permanent magnets over the entire diameter of the well is generated by the two identically directed permanent magnets in the well assigned thereto.

A very high, localized magnetic field is generated on the floor and/or on the walls of the wells of a microplate, which has the result that the majority of the magnetic particles are collected and retained in the immediate surroundings of the permanent magnets.

For all microplate types, the liquid may be suctioned out of the wells in such a way that a minimal residual volume of a few μl remains in the wells.

The suction points of a microplate are provided in all wells having identical geometry and positioning.

The so-called "crosswise suctioning" may be performed automatically and optimally at the lowermost point of the wells and/or on the periphery of the flat floor wells.

It does not play a role in the use of the microplate carrier according to the invention whether or not the floor of the microplate has openings between the wells (which are essential in the device according to U.S. Pat. No. 5,779, 907, for example).

BRIEF INTRODUCTION OF THE DRAWINGS

The present invention will be explained in greater detail on the basis of schematic drawings, which do not restrict the scope of the invention and only show preferred exemplary embodiments. In the figures.

DETAILED DESCRIPTION OF THE PRESENT INVENTION

Figure 1:
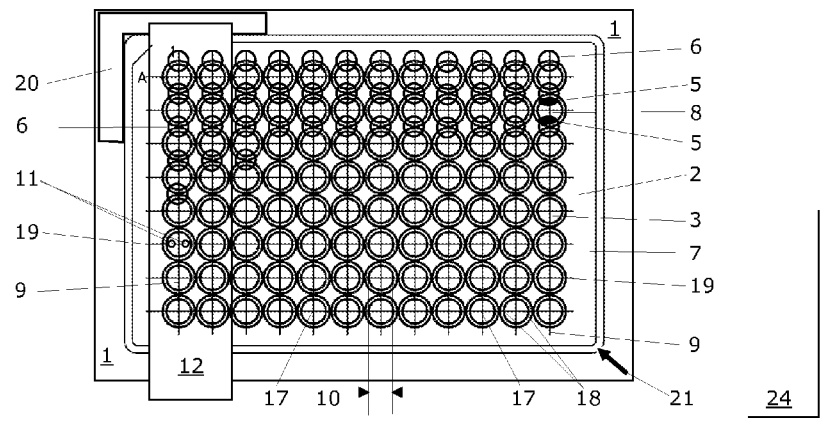
FIG. 1 shows a top view of a microplate carrier according to a first embodiment having 108 permanent magnets.

The FIG. 1 shows a top view of a microplate carrier 1 according to a first embodiment having 108 permanent magnets 6. The microplate carrier 1 is capable of receiving a microplate 2. In connection with the present invention, all multi-well plates having a plurality of wells or containers which is situated in an array are referred to as microplates. Especially preferred microplates have at least approximately the mass and the footprint of a microplate according to the SBS standard, as published by the American National Standards Institute (ANSI).

For example, microplates whose wells are equipped with a round floor, flat floor, or V floor are known. V floor wells having circular or square cross sections are known, so that the floor area is implemented as more conical or as pyramidal. The wells may be implemented as "normal wells" or also as "deep wells". Wells in the shape of truncated cones or truncated pyramids are also known per se. All microplates having greatly varying well shapes share the feature that they have a standardized area, i.e., a standardized "footprint", and the axial spacing of the particular wells situated in an array is also standardized. This axial spacing is, for example, 18 mm in 24-well (4×6) plates, 9 mm in 96-well (8×12) plates, and 4.5 mm in 384-well (16×24) plates. Magnetic particles 5 are located, suspended in a liquid 4, with or without samples adhering thereto in the wells 3 of such a microplate 2. The microplate carrier 1 comprises permanent magnets 6 generating magnetic fields, which are implemented to collect and retain the magnetic particles 5 on the floor and/or on the walls 7 of the wells 3 of this microplate 2. The microplate carrier 1 according to the present invention comprises two permanent magnets 6 situated diametrically opposite in relation to the well 3 for each well 3 of the microplate 2. These two permanent magnets 6 have the same polarity directed toward the well 3.

Because the influence of the magnetic field of many of these permanent magnets 6 situated in an array acts on two adjacent wells at a time, as may be seen from FIG. 1, all permanent magnets of the microplate carrier 1 are oriented identically. These two permanent magnets 6 per well 3 are preferably implemented as essentially cylindrical, the poles being located at the upper and lower circular surfaces of the cylinder standing essentially perpendicular to the footprint of the microplate to be placed. The magnetic axis 25 of all permanent magnets is thus at least essentially perpendicular to the surface of the placed microplate.

Each two permanent magnets 6 of the microplate carrier 1 according to the invention always generate an at least essentially particle-free space 8 in the well 3 assigned thereto. This essentially particle-free space 8 extends at least essentially over the entire diameter 10 of the well 3 transversely to an axis 9 connecting the two permanent magnets 6. This particle-free space 8 allows at least one cannula 11 of a microplate washing device 12 or a pipette tip 15 of a pipetting device 16 to be lowered into a well 3 and the liquid 4 to be aspirated out of this well 3, without a significant quantity of the magnetic particles 5 being suctioned using this cannula 11 or pipette tip 15.

The first embodiment of the microplate carrier 1 according to the invention comprises 108 permanent magnets 6, which are situated standing in 9 rows diametral to the wells 3 of a 96-well microplate 2. It is known that standard microplates have an 8×12 array of wells 3, all of these 96 wells having an axial spacing of 9 mm to one another and being situated in 8 rows (A-H) and in 12 columns (1-12). As shown, the well A1 is located at the top left. The columns are oriented along the column axes 9. In this first embodiment, the permanent magnets 6 are also oriented along these column axes 9. The centers of these preferably cylindrical permanent magnets are also spaced 9 mm apart from one another. These permanent magnets preferably comprise neodymium, iron, and boron (NdFeB) and have a diameter of 4 mm and a height of 5 mm. The flux density of these permanent magnets is very high in comparison to their dimensions and is preferably more than 1 Tesla. The magnets used in an exemplary embodiment have an effective flux density of 1.08 to 1.12 Tesla.

The permanent magnets 6 never come into direct contact with the liquids 4 or the magnetic particles 5 in the wells 3 and are preferably sunk approximately 2 mm into the plate-shaped microplate carrier 1. The microplate carrier 1 is preferably manufactured from a dimensionally-stable plastic, such as POM (polyoxymethylene or polyacetal). The microplate carrier 1 is preferably manufactured in the injection-molding method, the depressions for sinking the permanent magnets 6 preferably being left out. The permanent magnet cylinders are then inserted fitting into the corresponding depressions or glued into these depressions. A magnetizable metal plate (e.g., made of nickel or iron) (not shown) may also be fastened to the back of the microplate carrier 1, which helps to prevent the permanent magnets from falling out or unintentionally being pulled out of their depressions. In addition, the mounting of the permanent magnets in the microplate carrier 1 according to the invention is simplified by such a metal plate.

Preferably, so-called "paramagnetic beads" are used as the magnetic particles 5, as have been known for some time to those skilled in the art. In addition, a microplate washing device 12 and/or a washing head 12 of such a washing device is shown schematically as a rectangle in FIG. 1. Washing heads of this type are known and have an array of eight cannulas 11, for example, using which liquid 4 may be suctioned simultaneously out of all wells 3 of a column (column 1 here). A new liquid may then be introduced into these eight wells via the same or a further cannula. However, washing heads 12 are also known which each comprise 8, 16, or even 96 (i.e., 192 channels) or 384 suction and dispensing cannulas, so that suctioning may be performed simultaneously in all wells 3 of a microplate 2 and dispensing may be performed without changing the washing head 12. The use of such cannula arrays is particularly favored by the microplate carrier 1 according to the present invention, because the magnetic particles 5 or "beads" are collected and retained at identical locations on the floor and/or on the walls in each case in all wells 3 of the microplate 2. This obviously simplifies the control of the cannula array, because all cannulas 11 of a washing head 12 encounter exactly identical situation and geometry of the magnetic particle configuration. The identical optimum position for suctioning the liquid from the wells may thus be selected for all cannulas.

It is obvious that the best position of the cannulas for suctioning liquid out of wells having a round or V floor is the lowest point of the well 3, which is located in the center 17 of the well. The behavior is different in the flat floor wells, whether the flat floor relates to the entire diameter 10 of the well or only a reduced, central part of the floor of a well shaped like a truncated cone is flattened. With flat floors, suctioning is to be performed at the edge of the floor, i.e., in its periphery 18, so that an annular residual volume does not remain after the suctioning, which significantly impairs the washing efficiency.

The term "washing devices for microplates" is understood in connection with the present invention as devices, using which magnetic particles and/or biological samples, which are provided in free suspension or bound to the magnetic particles, may be washed in the wells of a microplate. The term "washing" comprises all known treatment steps of the magnetic particles and/or biological samples with liquids, such as buffer solutions.

The term "washing efficiency" is understood in the connection with the present invention as the ratio of the volume of the exchanged liquid to the volume of the original liquid remaining in the well after the washing step. The most complete possible exchange and/or the smallest possible component of the original liquid remaining in the well after the suctioning are desired.

Figure 2:
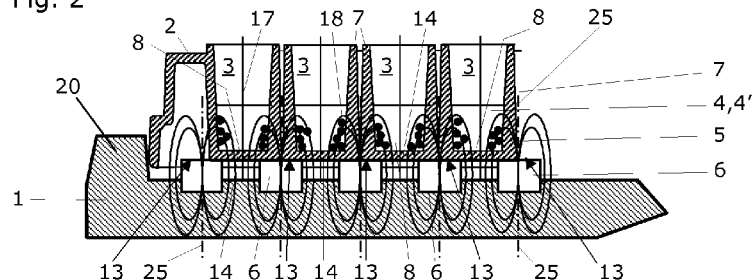
FIG. 2 shows a vertical partial section through the microplate carrier of FIG. 1 along a section line A-A.

The FIG. 2 shows a vertical section through the microplate carrier 1 of FIG. 1 along a section line A-A. The microplate carrier 1 according to the invention comprises permanent magnets 6 generating magnetic fields, which are implemented to collect and retain the magnetic particles 5 on the floor 14 and/or on the walls 7 of the wells 3 of this microplate 2. The microplate carrier 1 comprises two permanent magnets 6 situated diametrically opposite to one another in relation to the well 3 for each well 3 of the microplate 2, which have the same polarity directed toward the well 3. Each two permanent magnets 6 are implemented as essentially cylindrical, the north pole 13 or the south pole (not shown) always being located on the upper circular face of the cylinder. It actually does not play a role which pole is directed upward or downward; in contrast, it is essential that all permanent magnets 6 of the microplate carrier 1 according to the invention have an identically oriented polarity, and the magnetic axis 25 of the permanent magnets 6 is essentially perpendicular to the surface and/or to the footprint of the placed microplate 2.

In addition, the microplate carrier 1 preferably comprises a bulge 20 in one corner and a contact pressure unit 21 in the opposite corner. The microplate 2 lying on the upper circular faces of the permanent magnet cylinder 6 is pressed elastically against the bulge 20 using the contact pressure unit 21 and thus assumes a precisely defined position on the microplate carrier 1 without play.

Alternatively, centered fixing may be provided (not shown), as is known from patents EP 1 186 891 B1 and U.S. Pat. No. 7,054,001 B2 and is preferred above all for 384-well microplates.

The microplate carrier 1 may be implemented as a simple support plate (cf. FIG. 1). The microplate carrier may also be implemented as a carriage for a microplate washing device, as are known per se (cf. FIG. 2). Alternatively to these embodiments shown of a microplate carrier 1, it may also be implemented as a so-called "carrier", as are known for precisely defined carrying of three microplates on the surface of the worktable of a so-called "workstation", for example (not shown).

Such "workstations" are preferably automated systems for sample transfer and sample manipulation. In automatic systems, the user does not have to execute all individual treatment methods. A further shared feature of such known systems is that samples are often processed in standardized microplates. Such microplates are available in all possible formats, but typically comprise 96 sample vessels or "wells", which are situated in a regular 8×12 pattern having a 9 mm axial spacing. Microplates having a multiple (e.g., 384 wells) or also only a fraction (e.g., 24 wells) of this well count or density are also used. Different workstations may be connected by one or more robots for carrying the microplates. One or more robots moving in accordance with a coordinate system may be used for working on a worktable surface. These robots may carry plates or other sample containers and also transfer liquids. A central control system and/or a computer monitors and controls these known systems, whose outstanding advantage is the complete automation of the work process. As a result, such systems may be operated for hours and days, without human intervention being necessary.

The microplate carrier 1 shown in FIG. 2 generates an at least essentially particle-free space 8, which extends over essentially the entire diameter 10 of the flat floor well 3 of a microplate 2 transversely to an axis connecting the two permanent magnets 6, using the two permanent magnets 6 in the well 3 assigned thereto. Because of the high magnetic force of the preferably used NdFeB permanent magnets 6, the magnetic particles are already collected within a few seconds to a few minutes on the floor 14 and/or on the walls 3 and then retained at the location as long as the microplate 2 lies on the permanent magnets 6 of the microplate carrier 1 and the liquid 4 in the wells 3 is not subjected to any agitation, for example, an ultrasound treatment, shaking, or turbulence by inflowing liquid. The magnetic axis 25 of the permanent magnets 6 is well recognizable in FIG. 2.

Figure 3:
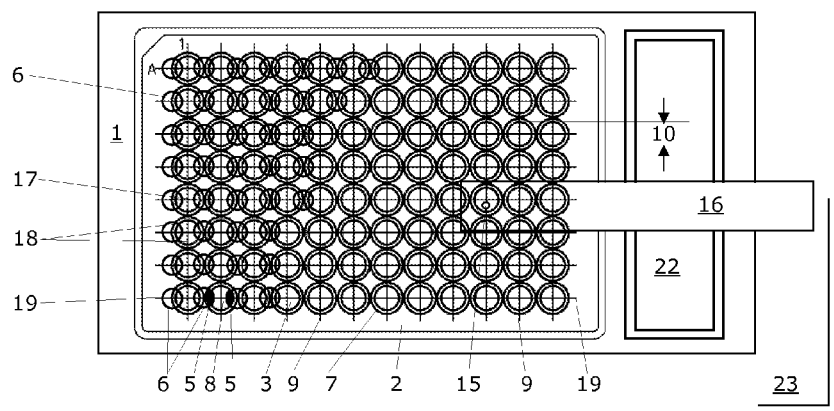
FIG. 3 shows a top view of a microplate carrier according to a second embodiment having 104 permanent magnets.

The FIG. 3 shows a top view of a microplate carrier 1 according to a second embodiment having 104 permanent magnets. This second embodiment of the microplate carrier 1 according to the invention comprises 104 permanent magnets 6 which are situated standing in 13 columns diametral to the wells 3 of a 96-well microplate 2. It is known that standard microplates have an 8×12 array of wells 3, all of these 96 wells having an axial spacing of 9 mm to one another and being situated in 8 rows (A-H) and in 12 columns (1-12). As shown, the well A1 is located at the top left. The rows are oriented along the row axes 19. The permanent magnets 6 are also oriented along these row axes 19 in the second embodiment. The centers of these preferably cylindrical permanent magnets are also spaced 9 mm apart from one another.

The microplate carrier 1 shown in FIG. 3 is implemented as a carriage of a so-called "washer", i.e., a microplate washing device 12, and comprises a trough 22 in which the medium used for the so-called "priming", i.e., the initial filling of the washer cannulas 11, is collected. The trough 22 shown has a width which allows the priming of the 16 or 32 cannulas of a 16-channel washer. However, an arm of a pipetting device 16 is also schematically shown, on which at least one pipette tip 15 is fastened. For working with larger systems, such as workstations, pipetting devices 16 are also used which comprise, for example, 8 pipette tips 15 which may be raised and lowered individually (not shown). Pipetting heads are also known which have 96 or 384 pipette tips, for example (not shown). The use of such pipette arrays in particular is favored by the microplate carrier 1 according to the invention, because the magnetic particles 5 or "beads" are collected and retained at identical locations in each case on the floor 14 and/or on the walls in all wells 3 of a microplate 2. This obviously simplifies the control of the pipette array, because all pipette tips 15 of a pipetting device 16 encounter an exactly identical situation and geometry of the magnetic particle positioning. The identical optimal position for suctioning the liquid out of the well may thus be selected for all pipette tips 15.

It is obvious that the best position of the pipette tips for suctioning liquid out of wells having a round or V floor is the lowest point of the well 3, which is located in the center 17 of the well. This is not true for the flat floor wells, whether the flat floor 14 relates to the entire diameter 10 of the well, or only a reduced, central part of the floor of a well shaped like a truncated cone is flattened. For flat floors, aspiration or suctioning is to be performed at the edge of the floor, i.e., in its periphery 18, so that no annular residual volumes remain after the suctioning, which significantly impair the yield.

Both embodiments shown support a method for processing microplates 2 in whose wells 3 magnetic particles 5, which are suspended in a liquid, with or without samples adhering thereto are located. In such a method, a microplate 2 is placed on a microplate carrier 1, the carrier 1 comprising permanent magnets 6 generating magnetic fields, using which the magnetic particles 5 are collected and retained on the floor 14 and/or on the walls 7 of the wells 3. The method according to the invention provides two permanent magnets 6 situated diametrically opposite in relation to the well 3 by the use of the microplate carrier 1 for each well 3 of the microplate 2, which have the same polarity directed toward the well 3.

As shown, an at least essentially particle-free space 8 is generated using the permanent magnets 6 of the microplate carrier 1 in each well 3 situated between them, which extends over at least essentially the entire diameter 10 of the well 3 transversely to an axis 9,19 connecting the two permanent magnets 6.

To wash the magnetic particles 5 with or without samples adhering thereto, at least one cannula 11 of a microplate washing device 12 is preferably lowered into this essentially particle-free space 8 in a well 3. The majority of the liquid 4 may then be aspirated, without a significant quantity of the magnetic particles 5 retained on the floor and/or on the walls 7 of the wells 3 of this microplate 2 being suctioned off by this cannula 11. The component of the residual liquid remaining in the wells is a few μl of the well contents.

In a next step, a liquid 4 is dispensed into each well 3 of the microplate 2 using at least one cannula 11 of the microplate washing device 12. The magnetic particles 5 retained on the floor 14 and/or on the walls 7 of the wells 3 of this microplate 2 are resuspended by the turbulence of the inflowing liquid 4.

Multiple repetitions of the two steps just described result in an effectively washed batch of magnetic particles 6 or beads. Samples adhering to the magnetic particles 6, such as proteins and/or nucleic acids, may also thus be effectively washed. The samples may subsequently be detached from the magnetic particles 6 or beads, i.e., eluted.

To elute the samples adhering to the magnetic particles 5, preferably at least one pipette tip 15 of a pipetting device 16 is lowered into this essentially particle-free space 8 in a well 3. A majority of the liquid 4 is then aspirated, without a significant quantity of the magnetic particles 5 retained on the floor and/or on the walls 7 of the wells 3 of this microplate 2 being suctioned off by this pipette tip 15.

In a next step, an eluent 4' (such as a solvent) is dispensed into each well 3 of the microplate 2 using at least one pipette tip 15 of the pipetting device 16, the magnetic particles 5 retained on the floor and/or on the walls 7 of the wells 3 of this microplate 2 being resuspended by the turbulence of the inflowing liquid 4 and the samples being detached from the magnetic particles.

The resuspension of the magnetic particles 5 or beads may be supported using a shaking device 24, onto which the microplate 2 is temporarily transferred.

Arbitrary method steps known per se to those skilled in the art may be executed hereafter, such as an incubation step, in which DNA suspended on the beads is thermally detached in an incubator at elevated temperature, for example. For example, the samples on the beads or in the eluent 4' may be assayed on the basis of fluorescence measurements and/or absorption measurements in a microplate reader 23. The samples may be provided as proteins, polypeptides, nucleic acids, or polynucleotides, for example. For further processing, the eluted samples may be transferred using a pipetting device 16 to at least one other well 3 of the same or another microplate 2. This further processing may be selected practically arbitrarily and comprises methods known per se such as polymerase chain reaction with nucleic acids or isotachophoretic assays on proteins, for example.

The placement of a microplate 2 on the microplate carrier 1 and/or the transfer of microplate carrier 1 and/or microplate 2 to a microplate washing device 12 or the transfer of the microplate 2 to a shaking device 24 or a reader 23 are each especially preferably executed using a computer-controlled robot arm.

Although up to this point only the washing of the magnetic particles and/or samples in a microplate washing device 12 and the elution of the samples from the beads using a pipetting device 16 have been described in detail, it is clear to those skilled in the art that samples may also be eluted in a microplate washing device 12 and magnetic particles and/or samples may be washed in the wells 3 of a microplate 2 using a pipetting device 16. This washing and elution may be performed manually or automatically in each case.

Identical features or elements of the microplate carrier 1 according to the invention are each provided with identical reference numerals, even if these elements are not described in detail in all cases. Combinations of the embodiments shown and/or described are within the scope of the present invention.

LIST OF REFERENCE NUMERALS 1 microplate carrier
2 microplate
3 well
4 liquid
4' eluent
5 magnetic particles, beads
6 permanent magnets
7 walls of the wells 8 essentially particle-free space
9 column axis
10 diameter of the wells
11 cannulas
12 microplate washing device, washing head
13 north pole
14 floor of the wells
15 pipette tip
16 pipetting device, pipetting head
17 center
18 periphery
19 row axis
20 bulge
21 contact pressure unit
22 trough
23 reader
24 shaking device
25 magnetic axis of the permanent magnets

What is claimed is:

1. A microplate washing device with a microplate carrier for carrying a microplate, the microplate having an array of wells and a footprint according to the SBS standard, as published by the American National Standards Institute, the wells comprising a center, a floor, and walls, the wells further comprising magnetic particles, the magnetic particles being suspended in a liquid with or without samples adhering thereto;
   wherein the microplate carrier comprises 108 permanent magnets generating magnetic fields to collect and retain the magnetic particles on the floor and/or on the walls of the wells of the microplate;
   wherein all of the permanent magnets of the microplate carrier have an identically oriented polarity and an upper face and a magnetic axis, which magnetic axis of each permanent magnet is at least essentially perpendicular to the footprint of the microplate;
   wherein the permanent magnets of the microplate carrier are situated so that for the microplate that is placed on the microplate carrier in a processing position, two of the permanent magnets are situated diametrically opposite in relation to each well of said microplate each well of the microplate being situated above the upper faces of the two permanent magnets of the microplate carrier assigned to said well; and
wherein all the permanent magnets of the microplate carrier have an identically-oriented polarity;
   wherein the permanent magnets are oriented with their magnetic axes along column axes 1 to 12 of a 96 well standard microplate placed on the microplate carrier, so that for each well of said microplate the well center is located in the middle between two adjacent permanent magnets arranged in the respective column axis and assigned to said well and that said two adjacent permanent magnets generate an at least essentially particle-free space in the well assigned thereto, the at least essentially particle-free space extending over essentially the entire diameter of the well transversely to a column axis connecting said two adjacent permanent magnets.

2. The microplate washing device according to claim 1, wherein the permanent magnets are essentially cylindrical, the north pole or the south pole being located on the upper circular face of the cylinder.

3. The microplate washing device according to claim 1, wherein the essentially particle-free space is implemented to allow a cannula of the microplate washing device to be lowered into a well and the liquid to be aspirated from this well, without a significant quantity of the magnetic particles being suctioned off by the cannula.

4. The microplate washing device according to claim 1, wherein the floor of the wells is selected from a group which comprises flat floors, round floors, and V floors.

5. A method for processing a microplate in the microplate washing device of claim 1, wherein the method comprising the steps of:
   placing a microplate having an array of wells and a footprint according to the SBS standard, as published by the American National Standards Institute, in whose wells magnetic particles, which are suspended in a liquid, with or without samples adhering thereto are located in a processing position on the microplate carrier of the microplate washing device;
   generating an essentially particle-free space in each well of the microplate by the two adjacent permanent magnets assigned to each well, the at least essentially particle-free space extending over essentially the entire diameter of the well transversely to a column or row axis connecting said two adjacent permanent magnets;
lowering at least one cannula of the microplate washing device into the essentially particle-free space in each well; and
   aspirating a majority of the liquid from each well, without a significant quantity of the magnetic particles retained on the floor and/or on the walls of the wells of the microplate being suctioned off by this cannula.

6. The method according to claim 5,
   wherein a re-suspension liquid is dispensed into each well of the microplate using at least one cannula of the microplate washing device, the magnetic particles retained on the floor and/or on the walls of the wells of this microplate being re-suspended by the turbulence of the inflowing liquid.

7. The method according to claim 6, wherein the re-suspension is supported using a shaking device, onto which the microplate is transferred.

8. The method according to claim 5, wherein, to elute the samples adhering to the magnetic particles, at least one suctioning cannula of the microplate washing device is lowered into the essentially particle-free space in each well, and a majority of the liquid is aspirated, without a significant quantity of the magnetic particles retained on the floor and/or on the walls of the wells of the microplate being suctioned off using the suctioning cannula.

9. The method according to claim 8, wherein an eluent is dispensed into each well of the microplate using at least one dispensing cannula of the microplate washing device, the magnetic particles retained on the floor and/or on the walls of the wells of this microplate being re-suspended by the turbulence of the inflowing eluent and the samples being detached from the magnetic particles.

10. The method according to claim 5, wherein the at least one cannula is lowered into the center of the well when the microplate comprises a round floor or V floor well, or onto the periphery of the well when the microplate comprises a flat floor well, to suction off the liquid.

11. The method according to claim 5,
   wherein the magnetic particles are collected and retained at identical locations on the floor and/or on the walls in each case in all wells of the microplate; and
   wherein the microplate washing device comprises a washing head with a cannula array of suctioning cannulas, all suctioning cannulas of the washing head encountering exactly identical situation and geometry of the magnetic particle configuration for suctioning the liquid from the wells.

12. A microplate washing device with a microplate carrier for carrying a microplate, the microplate having an array of wells and a footprint according to the SBS standard, as published by the American National Standards Institute, the wells comprising a floor and walls, the wells further comprising magnetic particles, the magnetic particles being suspended in a liquid with or without samples adhering thereto;

wherein the microplate carrier comprises 104 permanent magnets generating magnetic fields, the permanent magnets, each having a magnetic axis and an upper face, being configured to collect and retain the magnetic particles on the floor and/or on the walls of the wells of the microplate;

wherein all of the permanent magnets of the microplate carrier have an identically oriented polarity and the magnetic axis of each permanent magnet is at least essentially perpendicular to the footprint of the microplate;

wherein the permanent magnets of the microplate carrier are situated so that for the microplate that is placed on the microplate carrier in a processing position, two of the permanent magnets are situated diametrically opposite in relation to each well of said microplate, each well of the microplate being situated above the upper faces of the two permanent magnets of the microplate carrier assigned to said well; and wherein the permanent magnets are oriented with their magnetic axes along row axes A to H of a 96 well standard microplate placed on the microplate carrier, so that for each wells of said microplate the well center is located in the middle between two adjacent permanent magnets arranged in the respective row axis and assigned to said well and that said two adjacent permanent magnets generate an at least essentially particle-free space in the well assigned thereto, the at least essentially particle-free space extending over essentially the entire diameter of the well transversely to a row axis connecting said two adjacent permanent magnets.

13. The microplate washing device according to claim 12, wherein the permanent magnets are essentially cylindrical, the north pole or the south pole being located on the upper circular face of the cylinder.

14. The microplate washing device according to claim 12, wherein the essentially particle-free space is implemented to allow a cannula of a the microplate washing device to be lowered into a well and the liquid to be aspirated from this well, without a significant quantity of the magnetic particles being suctioned off by the cannula.

15. The microplate washing device according to claim 12, wherein the floor of the wells is selected from a group which comprises flat floors, round floors, and V floors.

* * * * *